US012569458B2

(12) United States Patent
Murdock

(10) Patent No.: US 12,569,458 B2
(45) Date of Patent: **\*Mar. 10, 2026**

(54) METHOD TO DELIVER ANTIFIBRINOLYTIC DRUGS TO MITIGATE DAMAGE TO THE BRAIN CAUSED BY CONCUSSIVE IMPACT

(71) Applicant: Murdock Technologies, LLC, Dallas, TX (US)

(72) Inventor: Frank Murdock, Dallas, TX (US)

(73) Assignee: Murdock Technologies, LLC, Dallas, TX (US)

( * ) Notice: Subject to any disclaimer, the term of this patent is extended or adjusted under 35 U.S.C. 154(b) by 533 days.

This patent is subject to a terminal disclaimer.

(21) Appl. No.: 18/094,870

(22) Filed: Jan. 9, 2023

(65) Prior Publication Data

US 2023/0149331 A1 May 18, 2023

Related U.S. Application Data

(63) Continuation of application No. 15/339,990, filed on Nov. 1, 2016, now Pat. No. 11,576,882, which is a continuation-in-part of application No. 14/848,923, filed on Sep. 9, 2015, now abandoned.

(60) Provisional application No. 62/050,247, filed on Sep. 15, 2014.

(51) Int. Cl.
| | |
|---|---|
| *A61K 31/195* | (2006.01) |
| *A61B 34/10* | (2016.01) |
| *A61B 34/20* | (2016.01) |
| *A61B 90/11* | (2016.01) |
| *A61K 9/00* | (2006.01) |
| *A61K 31/00* | (2006.01) |
| *A61K 41/00* | (2020.01) |
| *A61M 25/00* | (2006.01) |

(52) U.S. Cl.
CPC ............ *A61K 31/195* (2013.01); *A61B 34/10* (2016.02); *A61B 34/20* (2016.02); *A61B 90/11* (2016.02); *A61K 9/0014* (2013.01); *A61K 9/0019* (2013.01); *A61K 9/0085* (2013.01); *A61K 31/00* (2013.01); *A61K 41/0038* (2013.01); *A61M 2025/0042* (2013.01)

(58) Field of Classification Search
CPC .. A61K 31/195; A61K 9/0014; A61K 9/0019; A61K 9/0085; A61K 31/00; A61K 41/0038; A61B 34/10; A61B 34/20; A61B 90/11
See application file for complete search history.

(56) References Cited

U.S. PATENT DOCUMENTS

| | | | |
|---|---|---|---|
| 4,883,666 | A | 11/1989 | Sabel et al. |
| 7,022,125 | B2 | 4/2006 | Boethius |
| 2002/0049471 | A1 | 4/2002 | Boethius |
| 2007/0015837 | A1 | 1/2007 | Kun et al. |
| 2007/0224165 | A1* | 9/2007 | Guan ...................... A61P 25/00 514/18.2 |
| 2011/0142937 | A1* | 6/2011 | Macdonald .......... A61K 9/5078 514/561 |

OTHER PUBLICATIONS

Sawaya et al.; "Antifibrinolytic Therapy of Experimentally Grown Malignant Brain Tumors"; J. Neurosurg.; vol. 64 No. 2; Feb. 1986; pp. 263-268.
Kal et al.; "Response of rat prostate and lung tumors to ionizing radiation combined with the angiogemesis inhibitor AMCA"; Strahlenther Onkol; vol. 180 No. 12; Dec. 2004; pp. 798-804).
"Cyklokapron"; Label by Pfizer Inc.; published Jan. 2011; pp. 3-8.
"Effect of tranexamic acid in traumatic brain injury: a nested randomised, placebo controlled trial (CRASH-2 Intracranial Bleeding Study)"; BMJ 2011; Jul. 1, 2011; 14 pages.
"The Bottom Line"; CRASH-1; Summary; Aug. 15, 2014; 9 pages.
"The Lancet"; Crash 2 Report; Jun. 15, 2010; 32 pages.
Kageyama et al.; J. Neurosurg.; vol. 119; 2013; pp. 332-337.
Patterson et al.; Frontiers in Cellular Neuroscience; vol. 6 No. 58; 2012; pp. 1-10.
Kushimoto et al.; J. Neurotrama; vol. 20 No. 4; 2003; Abstract.
Napolitano et al.; J. Trauma Acute Care Surg .; vol. 74 No. 6; 2013; pp. 1575-1586.
Padovan et al.; J. of Biomed. Materials Research; vol. 73B No. 2; pp. 1-13.
Colorado Department of Education: Concussion Management Guidelines; Apr. 2014; pp. 1-53.

* cited by examiner

*Primary Examiner* — Jared Barsky
(74) *Attorney, Agent, or Firm* — Baker & McKenzie LLP

(57) ABSTRACT

Antifibrinolytic agents/drugs are applied to the concussive area of a patient's brain to counter the activation of a fibrinolytic process in the concussive area. Various techniques are described for administering the antifibrinolytic agent.

12 Claims, No Drawings

METHOD TO DELIVER ANTIFIBRINOLYTIC DRUGS TO MITIGATE DAMAGE TO THE BRAIN CAUSED BY CONCUSSIVE IMPACT

CROSS-REFERENCE TO RELATED APPLICATIONS

This application is a continuation of Ser. No. 15/339,990, filed Nov. 1, 2016, which is a continuation-in-part of Ser. No. 14/848,923, filed Sep. 9, 2015, which is based on provisional application Ser. No. 62/050,247, filed Sep. 15, 2014, all of the details of which are incorporated herein by reference thereto.

FIELD OF INVENTION

This invention relates to devices, methods and pharmacologic drugs and preparations for the inhibition of the growth of tumors and cancerous cells or to mitigate damage to the brain caused by concussive impact. In particular, the invention can act acutely and/or over an extended period of time to utilize/improve on the drug and preparation's anti-cancer/tumor performance, anti-inflammatory/anti-concussive capacity as well as its ability to enhance the radio sensitivity of the effected tissue.

BACKGROUND OF INVENTION

In the field of cancer treatments, several approaches are utilized; delivery of different pharmacologic compounds (such as chemotherapy), surgical excision and radiation treatments are current practice. These treatments are designed to remove well defined tumors and remove and mitigate the growth of diffuse and/or metastatic disease. In practice anti-cancer/tumor drugs are typically delivered systemically or locally and act to limit cancerous cell growth by encouraging cell death via toxicity. Common methods of cancer treatment typically involve a surgical excision of the tumor or cancerous area followed by subsequent treatments involving chemotherapy and/or radiation. It has long been the goal of cancer treatments to utilize surgical excision followed by direct local administration of an active anti-tumor agent such as the Gliadel wafer that can improve on the local control of the disease. Further it has long been a goal that the active anti-tumor agent might have immediate local anti-tumor impact and/or a controlled sustained release to extend the activity of the anti-cancer compound. Finally it has been a goal of cancer treatments to improve on radiation regimens by delivering a lethal radiation dose to the target area while minimizing the destructive effects of radiation to the surrounding healthy tissue. An improved approach to treating the disease would be to inhibit the spread of cancerous cells and to increase the sensitivity of the targeted. tissue to radiation so that dosages could be optimized and preferentially delivered (for example pre, intra, and/or post operatively) to a prescribed location.

Antifibrinolytic compounds such as tranexamic acid, aminoacaproic acid, aprotinin and new strategies such as kunitz type inhibitor polypeptide and similar polypeptide structures such as KD1 are typically delivered systemically (iv and/or oral) to control excessive bleeding primarily due to their ability to inhibit plasmin activation. U.S. Pat. No. 7,022,125 (all of the details of which are incorporated herein by reference thereto) discloses applying an antifibrinolytic agent to a substrate to effect hemostasis of a bleeding wound. Over the years they have also been briefly illustrated in the literature to potentially inhibit tumor growth and/or metastasis (possibly as a result of their ability to alter fibrin degradation which effects fibrinolytic pathways and tumor blood supply). In addition, antifibrinolytic agents have been shown to have an anti-inflammatory protective effect in tissue and to increase the radiosensitivity of some tumor cells. However, to date no surgical devices or methods have been described to utilize the anti-cancer, anti-inflammatory functionality of antifibrinolytic agents to improve on cancer and concussion treatments.

SUMMARY OF INVENTION

In accordance with this invention tumor growth and/or spread and brain injury caused by concussive impact is impeded and radio sensitivity of cancerous tissue is increased by administering an antifibrinolytic agent to the cancerous or injured area of the brain to restrain fibrinolytic activity in the area.

DETAILED DESCRIPTION

The present invention is based upon the realization that the body's response to trauma/surgery/disease involves the activation (local or otherwise) of the fibrinolytic process. In its broad aspect the invention is practiced by countering the fibrinolytic process through the administration of an antifibrinolytic agent to play an important role in improving treatments for these situations. In the situations of cancerous growths or brains subjected to concussive injury, that antifibrinolytic drugs if applied effectively (topically and/or systemically) in a manner which can act immediately and/or which extends their activity in the affected area over a period of time, will improve on the local control of the disease or injury and also in the case of cancer making the area more susceptible to the therapeutic and potentially curative effects of radiation.

The antifibrinolytic agent could be administered systemically, after surgical excision or could be injected where there is no excision into the cancerous area, such as via needle or catheter.

The inventive devices and methods are designed to improve cancer care by utilizing and improving the application of antifibrinolytic agents. One approach to the inventive treatment method would involve, surgical excision of the cancerous area, direct administration (such as via irrigation, needle injection or elution via a resorbable or non resorbable sponge) of an antifibrinolytic agent to the surgical area and/or the application of a pharmacologic preparation such as a hydrogel or resorbable wafer that would slowly release antifibrinolytic agents to retard the growth of the disease and concurrently make the area more radio sensitive over a period of time. The inventive methods and device could utilize the antifibrinolytic agent(s) that could be administered systemically (i.v. or oral) or directly (in open, endoscopic or topical procedures in its liquid injection form such as an irrigant or by needle injection) and/or via a time released or physically activated release (temperature, ph, or x-ray for example) of a preparation such as a biodegradable film, hydrogel, a sealant , biodegradable carrier such as, collagen, porcine gelatin, chitosan, fibrin, gellan gum or pectinor wafer (in similar fashion to Gliadel), liposomal drug delivery molecule or nano structured gels prior to surgical closure. Alternatively, or in addition to, antifibrinolytic drugs and preparations could be delivered by combining or constructing implanted devices such as transponding location beacons or rfd chips with coatings containing antifibrinolytics or other structures such as reservoirs that could release antifibrinolytic agents into the targeted area as well as via temporarily placed, biopsy cannulas (where the agent could be delivered prior to or post biopsy, for example, utilizing the needle cannula), catheters (similar to existing types that move csf for hydrocephalic patients) endovascular microcatheters (similar to those delivering embolic agents to aneurysms) and drug ports similar to morphine delivery for pain. Also, antifibrinolytic agents could be attached to molecules and strategies that are designed to seek out and attach themselves to cancerous tissue such as tumor fluorescence drugs. The device and method could be used during open surgical procedures such as tumor removal or debulking and/or delivered systemically and/or percutaneously and accurately (similar to the placement of deep brain stimulating electrodes), endovascular, via needle/cannula/catheter to preplanned (via historic image data or realtime images such as fluoroscopy, ultrasound, CT or MRI) clinical targets. Further, techniques that remove tissue such as biopsy or endoscopic debulking or place implants such as shunts for hydrocephalus or other objects into the body via needles or cannulas could also deliver antifibrinolytic agents before or after needle or cannula functions. Application of antifibrinolytic agents could be planned and optimized via surgical planning systems (which could predict the spread of the drug from a given insertion site by analyzing the targeted tissue via image data sets like MRI, as well as the molecular weight and diffusion characteristics of the delivered agent) and accurately delivered via real time imaging, image guided surgical navigation systems and stereotactic headframes and trajectory guides. Further, improved, inventive devices such as needles, cannulas and catheters (multi lumen and endovascular micro catheters for example) could be designed to best deliver the drug to the intended target while minimizing damage to healthy tissue that may occur during insertion.

This inventive method and device preparation centers on the innovative concept of improving cancer care by limiting the spread of cancerous/tumor cells by restraining fibrinolytic activity and increasing the radio sensitivity of the targeted area by placing antifibrinolytic agent(s) and/or related antifibrinolytic releasing devices such as catheters, needles and cannulas and/or drug releasing preparations, such as time released hyrdogels, drug eluting device coatings, biodegradable films and gelatins (porcine for example) and polymers such as chitsan into the body systemically and/or directly to affect clinically relevant areas such as brain, prostate, lung, liver or breast.

It is to be understood that systemic delivery could be optimized to deliver the agents to affected areas via time released formats (extended release pills for example) as well as improved delivery via nano or optimized particles to allow more of the agent to reach the intended target such as crossing the blood brain barrier to reach brain tumors or concussed brain areas for example.

Although the invention has been particularly described with regard to impeding tumor growth and increasing radio sensitivity of cancerous tissue, the invention is not limited to those applications. For example, the invention could be used to deliver antifibrinolytic drugs to treat concussions (mild head trauma). In that regard, the same activity is at play wherein the trauma, whether from disease, injury or surgery, brings about the biological response of heightened fibrinolytic activity and inflammation. The invention would serve to counter this activity by the application of a safe and effective amount of an antifibrinolytic agent(s).

Concussions (mild head trauma) occur in the U.S. several million times per year and typically are diagnosed by temporary changes in the patient's cognitive ability along with dizziness, sleepiness, sensitivity to light and headaches. Concussions are usually not visible with current radiographic study technology such as MRI or CT with no immediate signs of bleeding/or inflammation. However, it has been noted that the mechanical concussive force can lead to micro bleeds and linear tears in the brain as well as other pathophysiologic events and changes that can be delayed and/or take place over an extended period of time and it is expected that future technology will be better able to delineate affected tissue (and thus creating an opportunity to more specifically prescribe a treatment region). Current treatments consist of rest and limiting exposure to outside stimuli allowing the body to recover on its own. To date no pharmacologic treatment has been shown to be effective in treating concussions and their associated impact on the brain.

The inventive methods are designed to improve concussion care by utilizing the application of antifibrinolytic agents. A simple approach to the inventive treatment would be to administer a safe and effective amount of an antifibrinolytic agent as soon as possible after injury and diagnosis. An example being a concussive impact on a sports field, followed by diagnosis of concussion related symptoms, could be immediately treated with a simple pill form of an antifibrinolytic agent (such as or similar to tranexamic acid marketed as Lysteda in the U.S. for heavy menstrual bleeding). Another example would be an improved systemic/oral delivery of an antifibrinolytic agent that is designed in such a way that more of the drug passes through the blood brain barrier (such as nano technology) and thus more effectively reaches the affected area. The clinical impact being that the drug is being administered soon after injury and the resulting mitigation of fibrinolytic activity results in an improvement of symptoms and concussion related biomarkers and reduced incidence of pathophysiologic changes. More sophisticated approaches to treating with antifibrinolytics would utilize improved delivery strategies such as those previously described in cancer treatments to include controlled/extended release of oral as well as injected forms of the drugs. Further, implanted drug delivery depots such as gels could be employed to provide for extended treatment regimens.

Currently approved, safe and effective systemic doses of tranexamic acid, for example, are on the order of a maximum of 4 grams per day for 5 days delivered orally for heavy menstrual bleeding and approximately 3 grams per day (via 10% solution) for a maximum of 8 days delivered via IV injection to limit excessive bleeding in hemophiliacs undergoing tooth extraction. Effective anti-concussion doses, concentrations and regimens of antifibrinolytic agent(s) could be anticipated to deviate from these ranges (such as ¼ gram up to 6 grams or more per day until relevant biomarkers are back to within normal ranges) and could be delivered in improved delivery strategies like gels, extended release pills, nano-particles or implanted drug depots or local injection as long as they are effective and don't increase the incidence of thromboembolic events or other negative situations like retinal changes or seizure activity. Further, low maintenance doses could be anticipated as well as the brain recovers fully.

What is claimed:

1. A method for mitigating fibrinolytic activity, the method comprising:
   diagnosing a patient, having received an impact force to a head, with a concussion;
   topically administering an antifibrinolytic agent, selected from the group consisting of tranexamic acid and aminocaproic acid, to an area of the patient's brain to counter activation of a fibrinolytic process in the area.

2. The method of claim 1, wherein the antifibrinolytic agent is aminocaproic acid.

3. The method of claim 1, wherein the topically administering the antifibrinolytic agent is done via a technique selected from the group consisting of image guided surgical navigation systems, real time imaging, stereotactic headframes, trajectory guides, and endovascular micro catheters.

4. The method of claim 1, further comprising affected tissue.

5. The method of claim 1, wherein the antifibrinolytic agent is tranexamic acid.

6. The method of claim 1, wherein the topically administering the antifibrinolytic agent is done immediately after the diagnosing the patient for the concussion.

7. The method of claim 1, wherein the topically administering an antifibrinolytic agent is done at a dosage of the antifibrinolytic agent of up to 10 grams per day.

8. The method of claim 1, wherein the antifibrinolytic agent controls inflammation to protect tissue of the patient.

9. The method of claim 1, wherein the topically administering an antifibrinolytic agent is done at a dosage ranging from 25 grams per day to 6 grams per day.

10. The method of claim 1, wherein the impact to the head occurred during a sports activity.

11. The method of claim 1, wherein the patient had no visible bleeding during diagnosing the patient for the concussion.

12. The method of claim 1, wherein the topically administering the antifibrinolytic agent comprises multiple doses of the antifibrinolytic agent per day.

\* \* \* \* \*